United States Patent [19]

Stirling

[11] Patent Number: 4,652,527
[45] Date of Patent: Mar. 24, 1987

[54] PROCESS FOR CULTURING METHYLOPHILUS METHYLOTROPHUS

[75] Inventor: David I. Stirling, Summit, N.J.

[73] Assignee: Celanese Corporation, New York, N.Y.

[21] Appl. No.: 659,199

[22] Filed: Oct. 9, 1984

[51] Int. Cl.$^4$ .............................................. C12N 1/00
[52] U.S. Cl. ................................... 435/253; 435/155; 435/804
[58] Field of Search .................. 435/253, 804, 155

[56] References Cited

U.S. PATENT DOCUMENTS 3,989,594 11/1976 MacLennan et al. ................. 435/68

OTHER PUBLICATIONS

Beardsmore et al., (1982) J. Gen. Microbiol, vol. 128, pp. 1423–1439.
Atcc Media Handbook 1st Ed. 1984, p. 11.

*Primary Examiner*—Charles F. Warren
*Assistant Examiner*—M. Moskowitz
*Attorney, Agent, or Firm*—Depaoli & O'Brien

[57] ABSTRACT

This invention provides a process for single cell protein production which involves the culturing of *Methylophilus methylotrophus* microorganisms by facultative growth on glucose as a carbon and energy source.

5 Claims, No Drawings

PROCESS FOR CULTURING METHYLOPHILUS METHYLOTROPHUS

BACKGROUND OF THE INVENTION

The Imperial Chemical Industries Limited (ICI) protein producing *Methylophilus methylotrophus* microorganism is a Gram negative, nonpigmented rod with a single polar flagellum.

Early ICI publications suggested that newly discovered methanol utilizing strains corresponding to the subsequently named *Methylophilus methylotrophus* species could metabolize a variety of multi-carbon compounds as a sole source of carbon and energy. Such publications include British Pat. No. 1,370,892 and the "Identification Of A Methanol Oxidizing Pseudomonad" paper presented by D. Byrom and J. C. Ousby at the First International Symposium On Microbial Growth on $C_1$-Compounds (Tokyo, 1974); pages 23–27 (1975) in the proceedings published by Society of Fermentation Technology Osaka, Japan.

Later research by ICI scientists established that *Methylophilus methylotrophus* is an obligate methanol utilizing microorganism. In a paper entitled "Carbon Assimilation and Oxidation by Methylophilus Methylotrophus— The ICI SCP Organism" it states that "Contrary to earlier findings the organism is one of the few obligate methylotrophs so far described solely dependent on methanol for carbon and energy". This paper is published in the proceedings of The Second International Symposium On Microbial Growth On $C_1$-Compounds, 1977, by Scientific Center For Biological Research, USSR Academy Of Sciences, Puschino, Russia.

It would be advantageous to have processes for microbiological production of single cell protein which were sufficiently versatile to utilize inexpensive and readily available carbon sources other than methanol, with a high rate and yield of protein production and with an amino acid distribution suitable for use as a food supplement.

Accordingly, it is an object of this invention to provide a process for culturing a methylotroph microorganism with a carbon source other than a single carbon organic compound.

It is another object of this invention to provide a process for the production of single cell protein by culturing *Methylophilus methylotrophus* with a multicarbon growth source.

Other objects and advantages of the present invention shall become apparent from the accompanying description and examples.

DESCRIPTION OF THE INVENTION

One or more objects of the present invention are accomplished by a process for the production of a *Methylophilus methylotrophus* culture which comprises cultivating a strain of *Methylophilus methylotrophus* aerobically in an aqueous fermentation medium containing essential nutrients and between about 0.2–5 weight percent glucose, based on the total weight of the culture medium, as a growth carbon source.

As another embodiment, the present invention provides a process for production of single cell protein which comprises cultivating a strain of *Methylophilus methylotrophus* aerobically in an aqueous fermentation medium containing essential nutrients and between about 0.2–5 weight percent glucose as a facultative growth carbon source, and harvesting and drying the cell yield as a proteinaceous product.

As another embodiment, the present invention provides a single cell protein-producing bioconversion system comprising an aqueous fermentation medium containing essential nutrients, between about 0.2–5 weight percent glucose as a facultative growth carbon source, and an inoculum of *Methylophilus methylotrophus*.

Suitable bacterial strains for utilization in the present invention process are identified in U.S. Pat. No. 3,989,594, such as those assigned accession numbers NRRL B5352-5364, respectively, which correspond to strains NCIB 10508-15, respectively. *Methylophilus methylotrophus* Strain AS-1 (NCIB 10515;ATCC 53528) has exceptional properties for achieving the objects of the present invention.

The process can be conducted as a batch culture or single stage continuous culture or multiple stage continuous culture procedure. The product of the process is a single cell protein biomass comprising bacterial cells together with other metabolites such as amino acids, organic acids, nucleotides, and the like.

The biomass is essentially free of pigments, toxic substances, offensive odorants, and the like. The dried biomass is suitable as a protein source for the preparation of comestibles. p In the practice of the invention process, *Methylophilus methylotrophus* bacteria is cultured under aerobic conditions in a nutrient medium containing glucose as a source of growth carbon and energy, and additionally containing nitrogen and phosphorus sources and mineral salts.

The nitrogen sources in the culture medium can be ammonia, urea, ammonium salt, nitrate salt, or the like. The elementary nitrogen content usually is in the range between about 0.01–1 weight percent of the culture medium.

Also provided are inorganic sources of essential elements such as potassium, phosphorus, sulfur and magnesium. These elements can be included in the form of inorganic compounds such as potassium chloride, magnesium sulfate, potassium phosphate, phosphoric acid, and the like. It is preferred that the inorganic compounds are employed in quantities that provide at least the following weight percent in combinations:

$K^+$: 0.01–0.25
$Mg^{+2}$: 0.001–0.1
$PO_4^{-3}$: 0.01–0.5
$SO_4^{-2}$: 0.01–0.25

A suitable aqueous culture medium is described in U.S. Pat. No. 3,989,594, which patent specification is incorporated in its entirety herein by reference.

Glucose is the sole source of growth carbon. It is an essential aspect of the invention process that the glucose is provided in a quantity between about 0.2–5 weight percent based on the weight of aqueous bioconversion medium. At a glucose weight level less than about 0.2 weight percent (e.g., 0.1 weight percent), little or no cell growth occurs. At a glucose weight level greater than about 5 weight percent, cell growth is inhibited and the yield of biomass is reduced. A glucose quantity between about 0.5–2 weight percent yields optimal results.

The invention process is conducted in a well aerated fermenter which hold the culture medium containing glucose, nutrients, a strain of *Methylophilus methylotrophus*, and trace elements such as iron, copper and molybdenum salts.

The culture growth is conducted at a temperature between about 30°–42° C., preferably between about 35°–39° C. The aqueous culture medium is aerated with about 0.1–1.5 liters of air per liter of aqueous medium per minute.

The glucose concentration can be maintained in the required range by various procedures, such as by measuring the nitrogen consumption or by monitoring the carbon dioxide release. The quantity of glucose to be added incrementally or continuously is calculated in this manner.

For purposes of a continuous culture operation, an inoculum of bacteria is added to the aqueous medium containing glucose and the other nutrients. The inoculum is grown as a batch culture, and then transferred to continuous culture in a Chemostat type of fermenter. During fermentation, aqueous medium enters and leaves the fermenter at equal rates. It is desirable to operate the fermentation under nutrient limiting conditions to achieve a steady rate in the culture medium, e.g., by limiting the quantity of phosphorus or nitrogen in the fermentation system.

The pH of the culture medium is maintained at the optimal level by stepwise or continuous addition of a suitable reagent. Useful pH control reagents include sodium hydroxide, potassium hydroxide, disodium hydrogen phosphate, ammonia, sulfuric acid, hydrochloric acid, nitric acid, phosphoric acid, and the like.

The cell biomass is recovered in a conventional manner, such as by centrifugation with repeated water washes. The resultant crude product is a pasty biomass containing 50 to 90 percent by weight of water. Drying of the biomass is accomplished by drum driers, fluidized bed driers or spray driers.

The dried biomass contains 1–5 weight percent water and approximately 80–90 weight percent of crude single cell protein. This crude protein has an amino acid content between about 70–80 weight percent of amino acids, about half of which is constituted of essential amino acids.

As a further embodiment, the present invention provides an improved process for increasing the rate and yield of single cell protein production which comprises culturing *Methylophilus methylotrophus* with a mixture of methanol and glucose as a growth carbon source. The methanol and glucose are employed in a molar ratio between about 0.1–1:1 of methanol to glucose.

To illustrate the advantages of the improved process, after a fermentation period of 2–3 days *Methylophilus methylotrophus* Strain AS-1 yields between about 3–5 grams of dry cell weight per liter of aqueous culture medium when either methanol or glucose is the sole source of growth carbon. When the growth carbon source is a 1:1 mixture of methanol:glucose, the dry cell yield per liter of aqueous culture medium is between about 5–7 grams.

As noted previously, a *Methylophilus methylotrophus* bacterial strain has been established to be an obligate methanol utilizer. Hence, by definition the prospective use of a multi-carbon growth source is precluded in connection with *Methylophilus methylotrophus* microorganisms.

It is unexpected that the said *Methylophilus methylotrophus* could be induced to grow facultatively on glucose as a sole carbon source, to provide a high yield of cell culture per liter of aqueous bioconversion medium. Apparently, previous workers had employed less than about 0.5 weight percent of a carbohydrate such as glucose when screening organic compounds as potential sources of assimilable carbon. For purposes of the present invention, glucose is a unique carbon source for facultative growth of Strain AS-1 of *Methylophilus methylotrophus*.

The following examples are further illustrative of the present invention. The components and specific ingredients are presented as being typical, and various modifications can be derived in view of the foregoing disclosure within the scope of the invention.

EXAMPLE

This Example illustrates a process for the growth of a *Methylophilus methylotrophus* culture on glucose in accordance with present invention embodiments.

The medium employed for growth of the culture is an ammonium mineral salts medium (AMS) as described in the publication by H. Dalton and R. Whittenbury in Arch. Microbiol, 109, 147(1976).

A.

For purposes of comparison, the culture is grown on methanol employing a conventional procedure.

A flask is charged with 25 ml of AMS medium, and methanol (0.5% v/v) as the growth carbon source. The flask is then inoculated with 0.2 ml of a previously grown *Methylophilus methylotrophus* AS-1 (NCIB 10515;ATCC 53528) culture (AMS/0.5% methanol, v/v).

The flask is incubated at 37° C. in a shaking water bath. After growth has ceased (48 hours), i.e., there is increase in optical density measured at 540 nm, the dry cell weight of the culture is equivalent to 0.39 g/l.

B.

The procedure described in A above is repeated, except that the methanol is replaced with glucose (0.2% w/v) as the growth carbon source.

After culture growth has ceased (144 hours), the dry cell weight of the culture is equivalent to 0.37 g/l.

C.

The procedure described in A above is repeated, except that the methanol is replaced with an increased quantity of glucose (0.5% w/v) as the growth carbon source.

After culture growth has ceased (144 hours), the dry cell weight of the culture is equivalent to 0.44 g/l.

D.

The procedure described in A above is repeated, except that the methanol is replaced with an increased quantity of glucose (2.0% w/v) as the growth carbon source.

After culture growth has ceased (144 hours), the dry cell weight of the culture is equivalent to 0.49 g/l.

E.

The procedure described in A above is repeated, except that the methanol is replaced by a mixture of methanol (0.25% v/v) and glucose (0.25% w/v) as the growth carbon source.

After culture growth has ceased (48 hours), the dry cell weight of the culture is equivalent to 0.546 g/l.

What is claimed is:

1. A process for the production of a *Methylophilus methylotrophus* culture which comprises cultivating an AS-1 strain of *Methylophilus methylotrophus* aerobically in an aqueous fermentation medium containing essential nutrients and between about 0.2–5 weight percent glucose as a growth carbon source, and harvesting and drying the cell yield as a proteinaceous product.

2. A process in accordance with claim 1 wherein the fermentation is run as a continuous operation.

3. A process for the production of single cell protein which comprises cultivating an AS-1 (NCIB 10515; ATCC 53528) strain of *Methylophilus methylotrophus* aerobically in an aqueous fermentation medium containing essential nutrients and between about 0.2–5 weight percent glucose as a carbon source which induces facultative growth, and harvesting and drying the cell yield as a proteinaceous product.

4. A process for increasing the rate and yield of single cell protein production which comprises culturing an AS-1 (NCIB 10515; ATCC 53528) strain of *Methylophilus methylotrophus* with a mixture of methanol and glucose as a growth carbon source, and harvesting and drying cell yield as a proteinaceous product; wherein the increase in single cell protein production is in comparison to the use of either methanol or glucose as a sole source of growth carbon.

5. A process in accordance with claim 4 wherein the methanol and glucose are in a molar ratio between about 0.1–1:1 of methanol to glucose.

* * * * *